(12) United States Patent
Padhye et al.

(10) Patent No.: US 10,078,046 B2
(45) Date of Patent: Sep. 18, 2018

(54) T-PEEL TEST FIXTURE

(71) Applicant: Massachusetts Institute of Technology, Cambridge, MA (US)

(72) Inventors: Nikhil Padhye, Sunnyvale, CA (US); David M. Parks, Pembroke, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 14 days.

(21) Appl. No.: 15/139,888

(22) Filed: Apr. 27, 2016

(65) Prior Publication Data

US 2016/0327471 A1    Nov. 10, 2016

Related U.S. Application Data

(60) Provisional application No. 62/157,585, filed on May 6, 2015.

(51) Int. Cl.
    *G01N 19/04*     (2006.01)
    *G01N 3/08*     (2006.01)

(52) U.S. Cl.
    CPC ............... *G01N 19/04* (2013.01); *G01N 3/08* (2013.01)

(58) Field of Classification Search
    CPC .................................. G01N 19/04; G01N 3/08
    See application file for complete search history.

(56) References Cited

U.S. PATENT DOCUMENTS

| | | | | |
|---|---|---|---|---|
| 3,548,652 A | * | 12/1970 | Baranwal | G01N 19/04 73/150 R |
| 3,580,065 A | * | 5/1971 | Strittmater | G01N 19/04 73/150 R |
| 4,926,694 A | * | 5/1990 | Crews, Jr. | G01N 3/20 73/794 |
| 5,331,858 A | * | 7/1994 | Theller | B29C 65/18 73/827 |

(Continued)

FOREIGN PATENT DOCUMENTS

WO      2014/109199 A1      7/2014

OTHER PUBLICATIONS

[No Author Listed] 180 Degree Peel Test on Plastic Films. Instron, Illinois Tool Works Inc., 2014, 1 Page, as archived by the Wayback Machine on Mar. 22, 2014. Retrieved on Apr. 5, 2018 from <https://web.archive.org/web/20140322014536/http://www.instron.us:80/wa/solutions/Peel_Test_Plastic_Films.aspx>.

(Continued)

*Primary Examiner* — Son Le
*Assistant Examiner* — Marrit Eyassu
(74) *Attorney, Agent, or Firm* — Nutter McClennen & Fish LLP

(57) ABSTRACT

T-peel test fixture for a vertical test machine. The test fixture includes an upper grip for holding an arm of a peel specimen that has a hangover tail and a lower grip for holding the other arm of the peel specimen. A first rack is connected to a support hanger. The upper grip and the first rack move in a vertical direction at a selected speed. A second rack includ- (Continued)

ing a support plate located to support the specimen hangover tail is driven in the vertical direction at one-half the selected speed. The fixture thus supports the hangover tail so that symmetry is maintained with respect to gravity to suppress the interfering effect of gravity on a peel test.

24 Claims, 6 Drawing Sheets

(56) References Cited

U.S. PATENT DOCUMENTS

| | | | | |
|---|---|---|---|---|
| 6,584,858 | B1* | 7/2003 | Miyazawa | G01N 19/04 73/150 A |
| 2007/0204701 | A1* | 9/2007 | Stewart | G01N 19/04 73/827 |
| 2008/0202254 | A1 | 8/2008 | Deng et al. | |
| 2012/0103081 | A1* | 5/2012 | Hoshino | G01N 19/04 73/150 A |
| 2014/0326074 | A1* | 11/2014 | Van Voast | G01N 19/04 73/827 |

OTHER PUBLICATIONS

[No Author Listed] 3M™ VHB™ Tape Test—Dynamic T Peel. 3M UK & Ireland, Jun. 11, 2013, 3 Pages, YouTube video. Retrieved on Apr. 6, 2018 from <https://www.youtube.com/watch?v=K77-EPTSI-M>.
[No Author Listed] Adhesive Peel Fixtures. Instron, Illinois Tool Works Inc., 2014, 1 Page, as archived by the Wayback Machine on May 12, 2014. Retrieved on Apr. 6, 2018 from <https://web.archive.org/web/20140512114600/http://www.instron.us/wa/acc_catalog/prod_list.aspx?cid=406&cname=Adhesive%20peel%20fixtures>.
[No Author Listed] Adhesive Strength of Medical Packaging (ASTM F88). Instron, Illinois Tool Works Inc., 2014, 1 Page, as archived by the Wayback Machine on Jun. 5, 2014. Retrieved on Apr. 5, 2018 from <https://web.archive.org/web/20140605111331/http://www.instron.us/wa/solutions/Medical-Packaging-Peel-Test.aspx>.
[No Author Listed] ASTM D903-98 (Reapproved 2010), Standard Test Method for Peel or Stripping Strength of Adhesive Bonds, Oct. 2010, ASTM International, 3 Pages.
[No Author Listed] ASTM D905-08E1, Standard Test Method for Strength Properties of Adhesive Bonds in Shear by Compression Loading, Edited May 2009, Published Oct. 2008, ASTM International, 5 Pages.
[No Author Listed] ASTM D905-08 (Reapproved 2013), Standard Test Method for Strength Properties of Adhesive Bonds in Shear by Compression Loading, Oct. 2013, ASTM International, 5 Pages.
[No Author Listed] ASTM D906-98 (Reapproved 2011), Standard Test Method for Strength Properties of Adhesives in Plywood Type Construction in Shear by Tension Loading, Apr. 2011, ASTM International, 4 Pages.
[No Author Listed] ASTM D1876-08, Standard Test Method for Peel Resistance of Adhesives (T-Peel Test), Oct. 2008, ASTM International, 3 Pages.
[No Author Listed] ASTM D3330/D3330M-04 (Reapproved 2010), Standard Test Method for Peel Adhesion of Pressure-Sensitive Tape, Jul. 2010, ASTM International, 6 Pages.
[No Author Listed] ASTM D3807-98 (Reapproved 2012), Standard Test Method for Strength Properties of Adhesives in Cleavage Peel by Tension Loading (Engineering Plastics-to-Engineering Plastics), May 2012, ASTM International, 3 Pages.
[No Author Listed] ASTM D5868-01 (Reapproved 2014), Standard Test Method for Lap Shear Adhesion for Fiber Reinforced Plastic (FRP) Bonding, Mar. 2014, ASTM International, 2 Pages.
[No Author Listed] ASTM D6252/D6252M-98 (Reapproved 2004), Standard Test Method for Peel Adhesion of Pressure-Sensitive Label Stocks at a 90° Angle, Sep. 1998, ASTM International, 3 Pages.
[No Author Listed] ASTM D6252/D6252M-98 (Reapproved 2011), Standard Test Method for Peel Adhesion of Pressure-Sensitive Label Stocks at a 90° Angle, Apr. 2011, ASTM International, 3 Pages.
[No Author Listed] ASTM D6862-11, Standard Test Method for 90 Degree Peel Resistance of Adhesives, Jan. 2012, ASTM International, 6 Pages.
[No Author Listed] ASTM D7234-12, Standard Test Method for Pull-Off Adhesion Strength of Coatings on Concrete Using Portable Pull-Off Adhesion Testers, Oct. 2012, ASTM International, 9 Pages.
[No Author Listed] ASTM-F88 Standard Test Method for Seal Strength of Flexible Barrier Materials (Peel Test). Life Science Outsourcing, Inc., 2010, 2 Pages, as archived by the Wayback Machine on Apr. 5, 2015. Retrieved on Apr. 5, 2018 from <https://web.archive.org/web/20150405000019/http://lso-inc.com/medical-package-testing/astm-f88.html>.
[No Author Listed] ASTM F88/F88M-09, Standard Test Method for Seal Strength of Flexible Barrier Materials, Jul. 2009, ASTM International, 11 Pages.
[No Author Listed] How to Perform an Adhesive Strength T-Peel Test—ASTM D1876. ADMET Testing Systems, Jul. 23, 2010, 4 Pages, YouTube video. Retrieved on Apr. 6, 2018 from <https://www.youtube.com/watch?v=I1SWCqNnE7c>.
[No Author Listed] ISO 8510-2, Adhesives—Peel test for a flexible-bonded-to-rigid test specimen assembly—Part 2: 180° peel, ISO 8510-2:2006(E), Dec. 1, 2006, Second Edition, 12 Pages.
[No Author Listed] ISO 11339, Adhesives—T-peel test for flexible-to-flexible bonded assemblies, ISO 11339:2010(E), Feb. 15, 2010, Third Edition, 12 Pages.
[No Author Listed] ISO 14676, Adhesives—Evaluation of the effectiveness of surface treatment techniques for aluminium—Wet-peel test by floating-roller method, ISO 14676:1997(E), Jul. 15, 1997, First Edition, 12 Pages.
[No Author Listed] ISO 29862, Self adhesive tapes—Determination of peel adhesion properties, ISO 29862:2007 (E), Dec. 15, 2007, First Edition, 20 Pages.
[No Author Listed] Peel Resistance for Adhesives, T-Peel Test (ASTM D1876). Instron, Illinois Tool Works Inc., 2014. 1 Page, as archived by the Wayback Machine on Feb. 18, 2014. Retrieved on Apr. 5, 2018 from <https://web.archive.org/web/20140218083646/http://www.instron.us:80/wa/solutions/peel_test_adhesives_tapes_aslmd1876.aspx>.
International Search Report and Written Opinion for Application No. PCT/US2016/030368, dated Aug. 11, 2016 (9 Pages).
Kim, K.S., et al., Elastoplastic analysis of the peel test. International Journal of Solids and Structures, 1988;24(4):417-435.
Padhye, N., et al., A roll-bonding machine for polymeric films. American Society for Precision Engineering, 2014 Annual Meeting, vol. 59, 2014, pp. 357-360.
Peterson, Amy, Common Problems with Common Tests. ASI—Adhesives & Sealants Industry, BNP Media, Jan. 2, 2014, 5 Pages. Retrieved on Apr. 5, 2018 from <https://www.adhesivesmag.com/articles/92564-common-problems-with-common-tests>.

\* cited by examiner

| S. No. | T-peel Specimen* | % Error * |
|---|---|---|
| 1 | Roll Bonded Laminates | 85.65 |
| 2 | Duct-Tape | 6.88 |
| 3 | Scotch-Tape | 7.35 |
| 4 | Teflon-EVA-Teflon | 31.79 |
| 5 | Teflon-silicone-encapsulant-Teflon | 24.41 |
| 6 | Vinyl-Vinyl | 3.51 |
| 7 | VinylLamate1-VinylLaminate1 | 7.46 |
| 8 | VinylLamate2-VinylLaminate2 | 1.19 |

$$* \%Error = \frac{|Avg.\ Force\ with\ Fixture - Avg.\ Force\ without\ Fixture|}{Avg.\ Force\ with\ Fixture}$$

FIG. 13

T-PEEL TEST FIXTURE

This application claims priority to provisional application Ser. No. 62/157,585 filed May 6, 2015, the contents of which are incorporated herein by reference in their entirety.

BACKGROUND OF THE INVENTION

This invention relates to a mechanical fixture enabling an accurate T-peel test of thin and flexible adhered laminates.

A peel test is a simple and popular mechanical test for measuring adhesion strength in a variety of applications, particularly for use with bonded thin and flexible laminates, and carried out in several different ways. The geometry usually consists of a laminate bonded to another laminate or to a thick substrate and the test is conducted by pulling the laminate off the other laminate or substrate at some angle, while recording the peeling-force in the steady-state debonding. The usual goal is to relate the experimentally obtained peel force to the intrinsic toughness of the interface, where the toughness of the interface represents the work required per unit area to advance a crack at the interface and has the units of $J/m^2$ or N/m. Only in very restricted scenarios can the peel force give a direct estimate of interface toughness. More generally, the peel force is affected by the geometry of the samples, the constitutive properties of the laminates, inter-facial properties, etc.

Depending upon the application, several existing ASTM standards such as ASTM D903-98(2010). ASTM D3807-98 (2012), ASTM D6252, ASTM D1876-08, ASTM D3330, ASTM D6862, ASTM F88/F88M-09 or ISO standards ISO 11339:2010, ISO 8510-2:2006, ISO 14676:1997, ISO 29862:2007 are commonly employed for measurement of adhesion through peeling. These standards can be easily practiced on various commercially available fixtures, for e.g. 90 Degree, 180 Degree, Climbing Drum, Floating Roller, Adjustable Angle, German Rotating Wheel, etc. peel fixtures. The present invention deals with a particular kind of peel test, known as T-peel test (T indicating that the specimen forms a T-like shape between symmetrical interfaces).

The T-peel test is quite straightforward to perform: the unbonded parts of two flexible laminates are clamped in the grips of a mechanical tester and separated apart. If the test is performed on a vertical mechanical tester, the bottom grip is usually held fixed while the top grip moves upwards. On vertical test machines, when T-peel specimens are thin and flexible, the action of gravity can lead to an asymmetric configuration. In this situation, the bending of the freely suspended end (hangover tail) and the degree of anti-symmetry introduced depends upon the geometry (length, width and thickness) and the material properties (density, modulus, etc.) of the specimens.

In critical scenarios, the bending action of gravity can plausibly induce plastic deformation in the lower peel arm in addition to a mixed-mode failure. All these effects can lead to a deviation in the measured peel force compared to an ideal and symmetrical T-peel. The uncertainty in the asymmetry during such a test is uncontrolled, degree of mode-mixity (or phase angle) is unknown, and thus no straightforward correction is possible. These issues lead to an uncertain estimation of inter-facial fracture toughness. In recent years, there have been some studies on the role of asymmetry in T-peel specimens, and a proposal of a testing apparatus to perform the T-peel in a layout such that the tail of the specimen aligns with gravity. However, in this configuration undesired twisting and bending of the T-peel specimen also occurs. In some cases the recommendation to compensate for the tail hangover during a peel-test is through hand-support. It is quite obvious that any such manual endeavor is not robust.

A principal object of this invention, therefore, is to provide a new and improved fixture and technique for a T-peel test that eliminates the limitations of prior T-peel test methods.

A further object of this invention is to provide a novel design of a mechanical fixture to support a freely suspended end of a T-peel specimen and thereby suppress the effect of gravity.

SUMMARY OF THE INVENTION

The T-peel test fixture for a vertical test machine according to the invention includes an upper grip for holding an arm of a peel specimen that has a hangover tail. A lower grip for holding the other an arm is provided and a first rack is attached to a support hanger and the support hanger is connected to a vertical machine. The upper grip and the first rack move in a vertical direction at a selected speed. A second rack is provided that includes a support plate attached thereto located to support the specimen hangover tail in which the second rack is driven in the vertical direction at one-half the selected speed. In this way, symmetry of the hangover tail is maintained and the effect of the gravity is suppressed. In a preferred embodiment, a gear train includes two spur gears, one spur gear having twice as many teeth as the other spur gear to provide the speed differential between the first and second racks.

During a peel test, the support plate moves in a kinematically desired manner such that symmetry of the T-peel specimen is maintained during the test. If the upper grip is movable and the lower grip is fixed then the mechanical fixture includes a gear-train (with a reduction ratio of 2:1), such that a support moves at a speed half that of the upper-grip. This speed differential can be achieved by, but not limited to, a set of racks and spur gears. The position of the mechanical fixture and/or the position of the support plate can be adjusted easily with respect to the testing frame or the test-specimen. The mechanical fixture can be mounted on, but not limited to, the testing frame. The mechanical fixture and/or support can me made of any suitable material.

BRIEF DESCRIPTION OF THE DRAWING

FIG. 13 is a chart summarizing the results of experiments with different adhered systems.

DESCRIPTION OF THE PREFERRED EMBODIMENT

Figure 1:
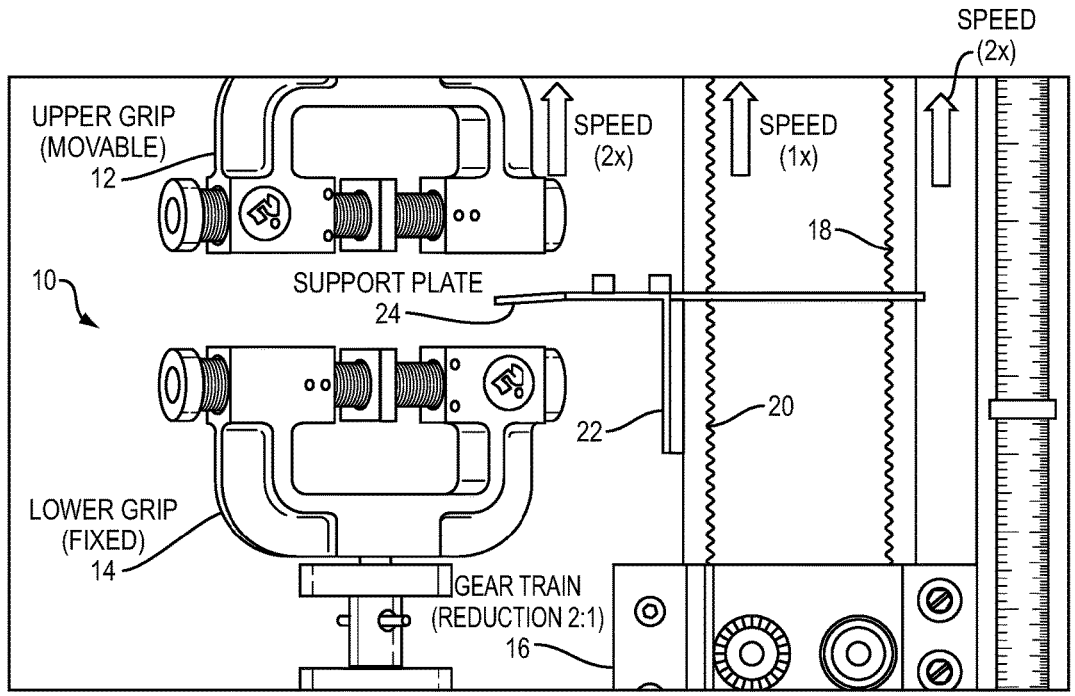
FIG. 1 is a plan view of the fixture of the invention mounted on a vertical testing machine.

With reference first to FIG. 1, the fixture 10 of the invention includes a movable upper grip 12 and a lower fixed grip 14. A gear train or gear box 16 includes a driving rack 18 that is attached to a support hanger 38 (see FIG. 2 for the support hanger 38), and the support hanger 38 is attached to a test machine. The test machine also carries the upper grip 12, and moves the driving rack 18 and the upper grip 12 in a vertical direction. A driven rack 20 is driven by the gear box 16 to move vertically at a rate of one-half the rate of the driving rack 18. The driven rack 20 includes a bracket 22 that carries a support plate 24. The support plate 24 is provided to support an over-hanging tail of a peel test specimen. Because the rack 18 moves at twice the speed of the rack 20, the support plate 24 will move upwardly in a way to keep an over-hanging tail horizontal so as to eliminate asymmetries as a result of gravity.

The mechanical fixture 10 shown in FIG. 1 can be sized, modified and retrofitted with a wide range of testing machines and is not limited to the embodiment shown in the figure.

Figure 2:
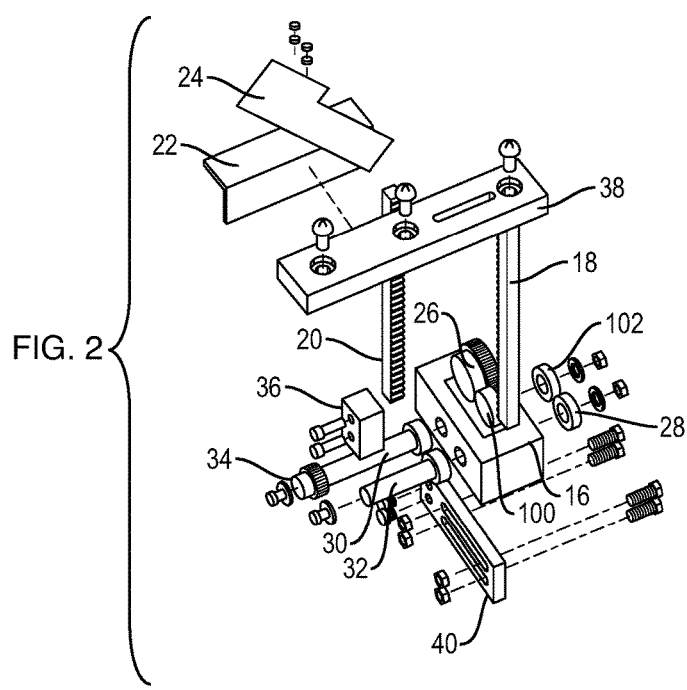
FIG. 2 is an exploded view of the mechanical fixture disclosed herein illustrating its various components.

With reference now to FIG. 2, the driving rack 18 engages with a spur gear 100 that includes, in this embodiment, 12 teeth. Bearing 28 supports the shaft 32. Bearing 102 supports the shaft 30. Shafts 32 and 30 drive the spur gears 100 and 26, respectively. The spur gear 26 has 24 teeth in this embodiment. A spur gear 34 has 12 teeth and is attached to the shaft 30 so that the driven rack 20 moves at half the speed of the driving rack 18. A rack retainer 36 supports the driven rack 20. A top support hangar 38 is actually connected to a testing machine, and supports the driving rack 18 which in turn drives the gear train and driven rack 20 and thereby raising the support plate vertically at a half speed.

When the upper grip 12 and the driving rack 18 move at a speed 2V, the driven rack 20 moves at speed V. A tail 48 of a test specimen (sec FIG. 3) rests on the support plate 24 during a test thus preserving symmetry. The gear box 16 can be attached to a testing frame with use of the support bracket 40. The position of the gear box 16 and support plate 24 can be adjusted easily in all directions with the provision of slots and grooves on the various support elements.

Figure 3:
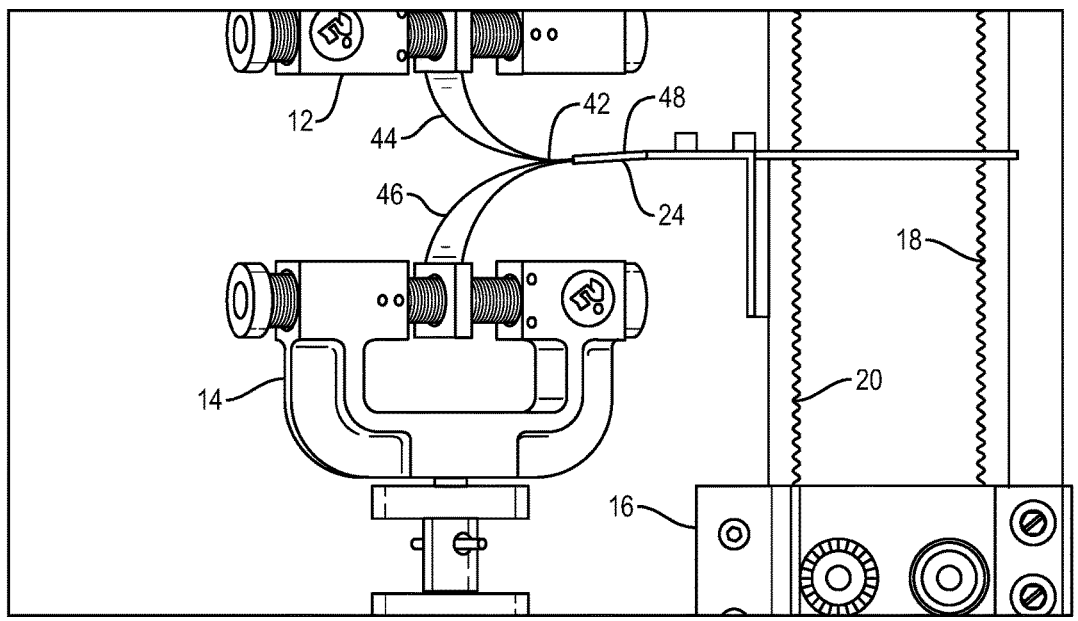
FIG. 3 is a plan view of the fixture disclosed herein during a T-peel test with the specimen hangover tail supported on a support.

As mentioned above, FIG. 3 illustrates the operation of the present invention. In FIG. 3, a specimen 42 includes an upper arm 44 and a lower arm 46. The upper arm 44 is grasped by the upper grip 12 and the lower arm 46 is grasped by the lower grip 14. The specimen 42 has the hangover tail 48 that rests on the support plate 24.

Figure 4:
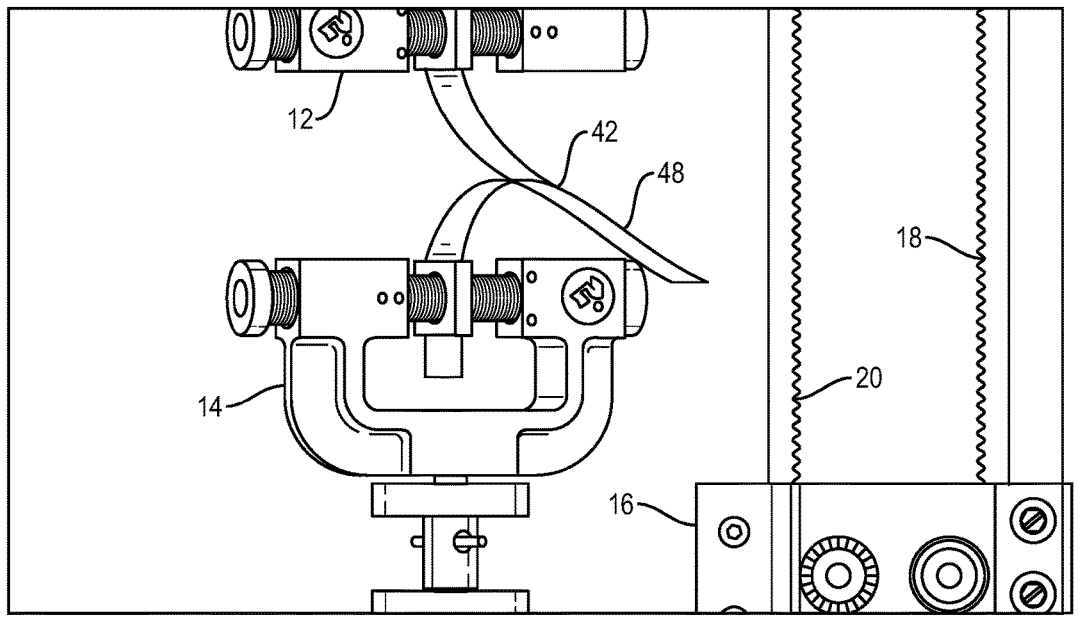
FIG. 4 is a plan view of the fixture disclosed herein without a support for the hangover tail showing that gravity causes an asymmetry during the test.
Figure 5:
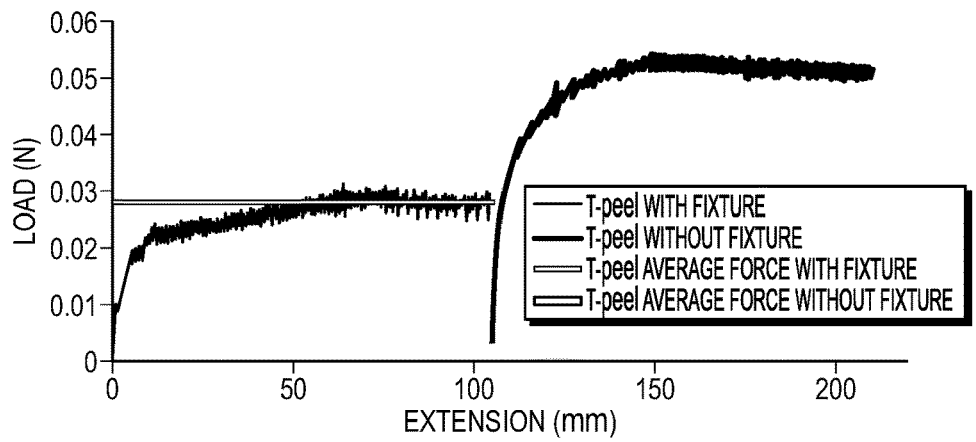
FIG. 5 is a graph of load versus extension comparing T-peel force with and without the use of the fixture of the invention on roll-bonded laminates.
Figure 6:
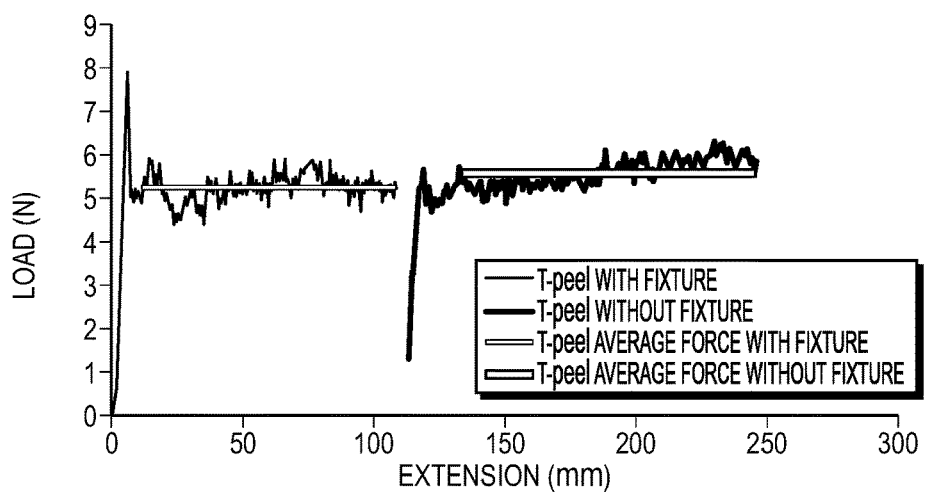
FIG. 6 is a graph of load versus extension comparing T-peel force with and without the use of the fixture of the invention on commercial duct tape.
Figure 7:
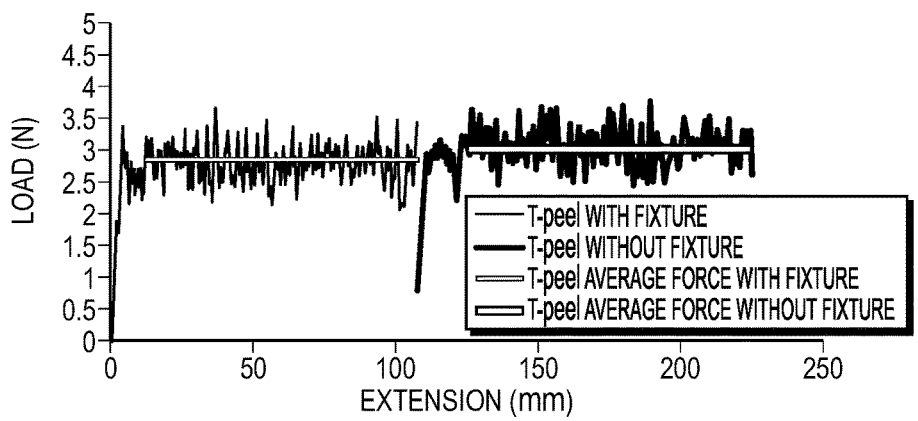
FIG. 7 is a graph of load versus extension comparing T-peel force with and without the use of the fixture of the invention on commercial Scotch tape.
Figure 8:
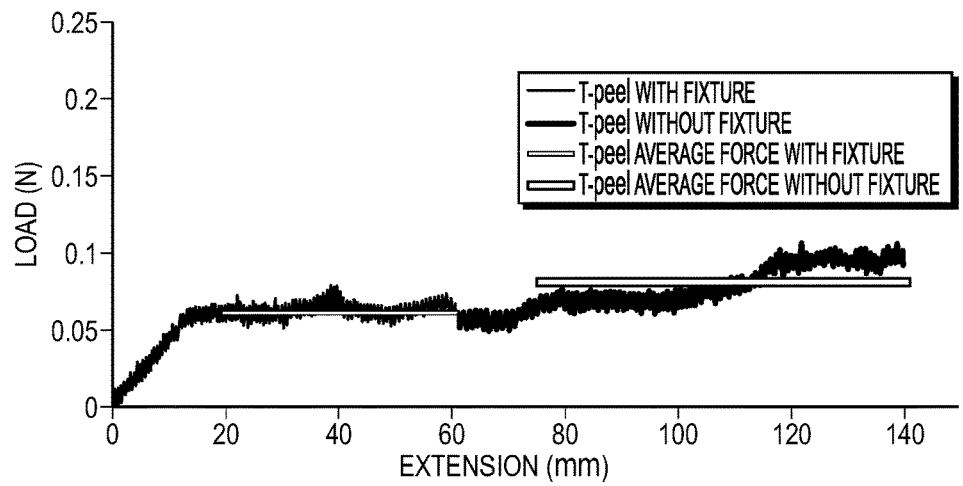
FIG. 8 is a graph of load against extension comparing T-peel force with and without the use of the fixture of the invention on a Teflon-EVA-Teflon system.
Figure 9:
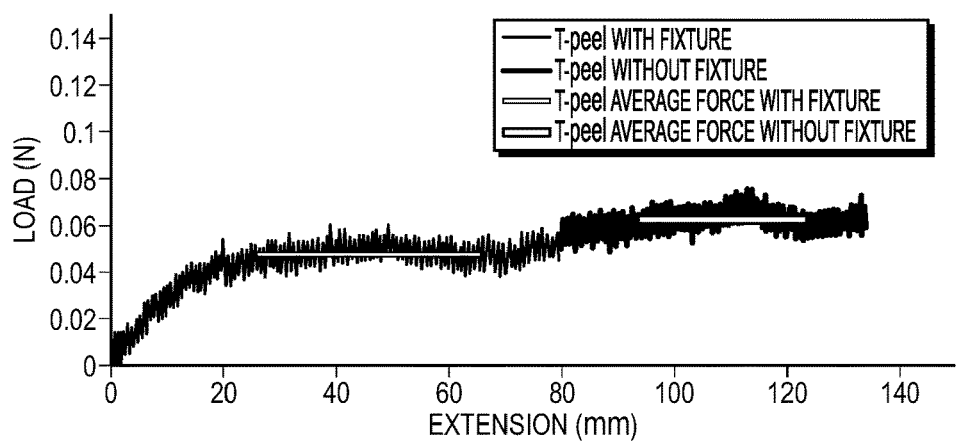
FIG. 9 is a graph of load versus extension comparing T-peel force with and without the use of the fixture of the invention on a Teflon-silicone-encapsulant-Teflon system.
Figure 10:
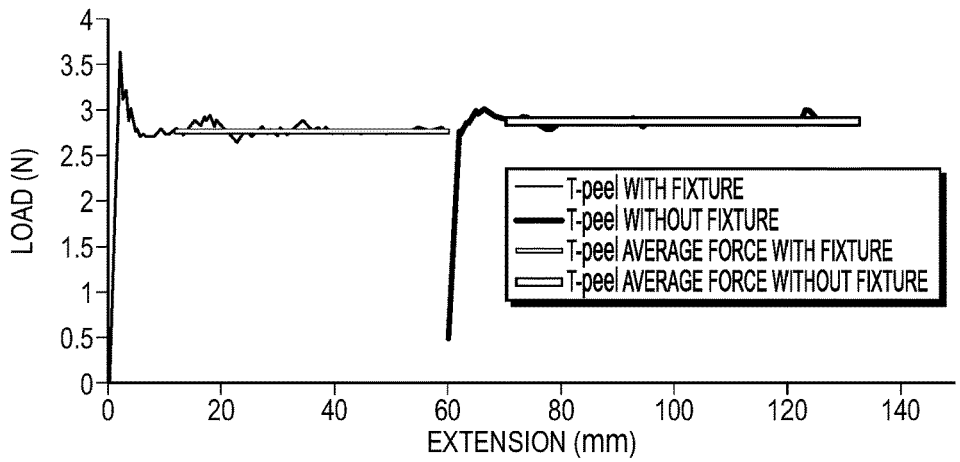
FIG. 10 is a graph of load versus extension comparing T-peel force with and without the use of the fixture of the invention on a vinyl-vinyl system.
Figure 11:
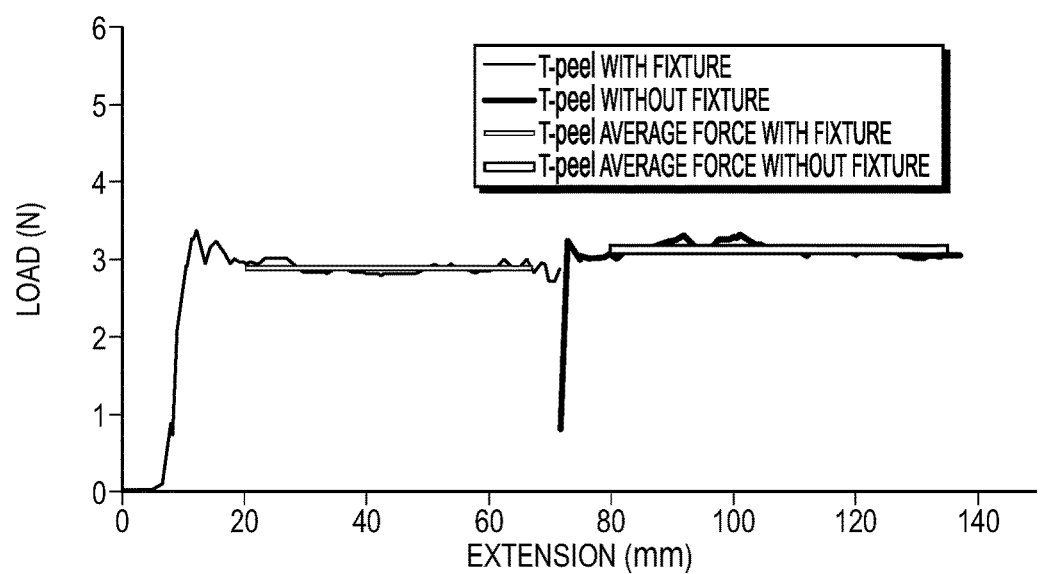
FIG. 11 is a graph of load versus extension comparing T-peel force with and without the use attic fixture of the invention on vinyl laminate 1-vinyl laminate 1.
Figure 12:
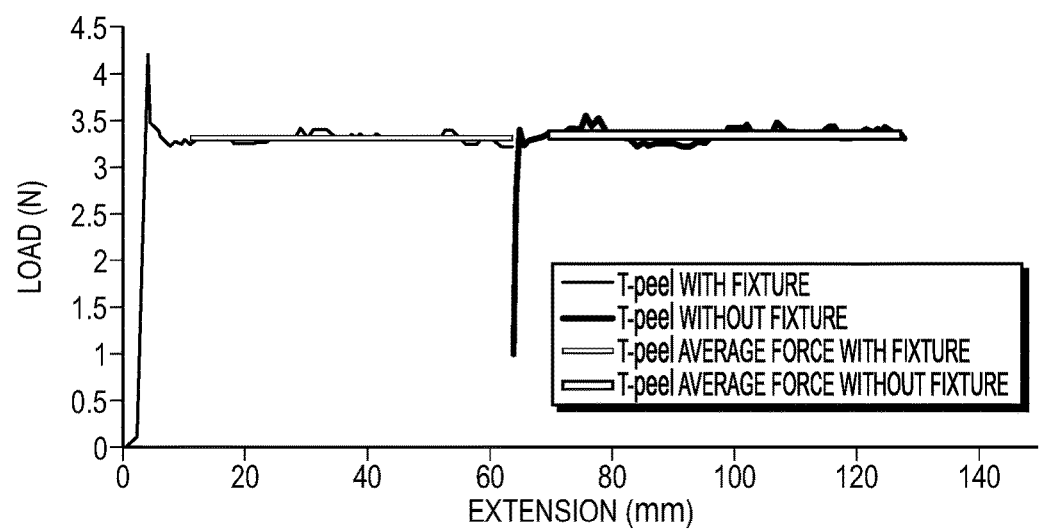
FIG. 12 is a graph of load versus extension comparing T-peel force with and without the use of the fixture of the invention on vinyl laminate 2-vinyl laminate 2.

FIG. 4 illustrates a situation when the support plate 24 of the present invention is not in use. As can be seen, the hangover tail 48 of the specimen 42 deflects under the influence of gravity resulting in an asymmetry that interferes with an accurate peel force measurement.

FIGS. 5-12 illustrate the efficacy of the fixture of the invention by comparing the T-peel force measured with and without the support plate of the invention. It is seen that in each case the average T-peel force without the use of the fixture of the invention is large leading to an overestimation of adhesive fracture energy. The fixture of the invention also prevents parasitic effects of twisting, shaking, flipping, etc. which can occur when the hangover tail of a test specimen is not supported. It will be apparent to those of ordinary skill in the art that design modifications can be made to the support plate to eliminate any further unwanted effects of air currents on the testing of extremely delicate and highly sensitive specimens. An example might be the presence of a channel on the support plate in which the specimen tail can reside.

The fixture of the invention is suitable for use with laminates that are extensible so long as energy stored due to elastic deformation is properly accounted for. The fixture disclosed herein may also be employed for use with asymmetrically bonded laminates.

Those of skill in the art will recognize that the 2:1 speed reduction could be accomplished with servo motors or other electrical or magnetic mechanisms.

It is recognized that modifications and variations of the invention will be apparent to those of ordinary skill in the art and it is intended that all such modifications and variations be included within the scope of the appended claims.

What is claimed is:

1. T-peel test fixture for use with a vertical test machine comprising;
    an upper grip for holding an arm of a peel specimen that has a hangover tail;
    a lower grip for holding the other arm of the peel specimen;
    a first rack attached to a support hanger, wherein the first rack and the upper grip move in a vertical direction at a selected speed; and
    a second rack including a support plate located to support the peel specimen hangover tail, the second rack being driven in the same vertical direction as the first rack at one-half the selected speed;
    whereby symmetry of the hangover tail is maintained to suppress the effect of gravity.

2. The T-peel test fixture of claim 1, wherein a gear train drives the racks and includes two spur gears, one spur gear having twice as many teeth as the other spur gear.

3. The T-peel test fixture of claim 1, wherein at least one of the upper grip and the lower grip are configured to hold the respective arm by grasping the respective arm of the peel specimen.

4. The T-peel test fixture of claim 3, wherein grasping the respective arm of the peel specimen further comprises clamping the respective arm of the peel specimen.

5. The T-peel test fixture of claim 1, further comprising:
    a first gear driven by a first shaft, the first gear being coupled to the first rack and having a plurality of teeth;
    a second gear driven by a second shaft, the second gear having a plurality of teeth that is twice the amount of teeth as the first gear; and
    a third gear coupled to the second shaft and the second rack, the third gear having a plurality of teeth that is half the amount of teeth as the second gear such the second rack is driven in the vertical direction at one-half of the selected speed of the first rack.

6. The T-peel test fixture of claim 1, wherein the T-peel test fixture is configured such that testing of the peel specimen occurs in only a single mode.

7. The T-peel test fixture of claim 1, wherein the support plate is configured to support the hangover tail of the peel specimen by supporting the peel specimen across at least a quarter of the length of the peel specimen to suppress the effect of gravity.

8. A test fixture, comprising:
an upper grip for engaging a first arm of a peel specimen that has a hangover tail;
a lower grip for engaging a second arm of the peel specimen;
a first rack attached to a support hanger, the first rack and the upper grip being configured to move vertically such that the movement is substantially perpendicular to a longitudinal axis extending through a substantial length of the peel specimen;
a second rack configured to move vertically such that the movement is substantially perpendicular to the longitudinal axis extending through a substantial length of the peel specimen, the second rack having a longitudinal axis that extends vertically along a length of the second rack; and
a support plate coupled to the second rack, the support plate having a length that extends substantially perpendicular to the longitudinal axis of the second rack such that a face of the plate that likewise has a length that extends substantially perpendicular to the longitudinal axis is configured to support the hangover tail of the peel specimen by supporting the peel specimen across at least a quarter of the length of the peel specimen.

9. The test fixture of claim 8, further comprising a gear train configured to drive the first and second racks, the gear train including at least two spur gears, one spur gear having twice as many teeth as the other spur gear.

10. The test fixture of claim 8, wherein the test fixture is configured to perform a T-peel test in which the peel specimen forms a T-like shape between symmetrical interfaces during operation of the test fixture with the peel specimen.

11. The test fixture of claim 8, wherein at least one of the upper grip and the lower grip are configured to hold the respective arm by grasping the respective arm of the peel specimen.

12. The test fixture of claim 11, wherein grasping the respective arm of the peel specimen further comprises clamping the respective arm of the peel specimen.

13. The test fixture of claim 8, further comprising:
a first gear driven by a first shaft, the first gear being coupled to the first rack and having a plurality of teeth;
a second gear driven by a second shaft, the second gear having a plurality of teeth that is twice the amount of teeth as the first gear; and
a third gear coupled to the second shaft and the second rack, the third gear having a plurality of teeth that is half the amount of teeth as the second gear such the second rack is driven in the vertical direction at one-half of the selected speed of the first rack.

14. The test fixture of claim 8, wherein the test fixture is configured such that testing of the peel specimen occurs in only a single mode.

15. The text fixture of claim 8, wherein supporting the peel specimen across at least a quarter of the length of the peel specimen suppresses the effect of gravity.

16. A test fixture, comprising:
an upper grip for engaging a first arm of a peel specimen that has a hangover tail;
a lower grip for engaging a second arm of the peel specimen;
a first rack attached to a support hanger and having a first longitudinal axis extending through a substantial length thereof, the first rack being configured to move vertically along a length of the first longitudinal axis with the upper grip moving in a same direction as the first rack;
a second rack disposed substantially parallel to the first rack such that a second longitudinal axis extending through a substantial length of the second rack is substantially parallel to the first longitudinal axis, the second rack being configured to move vertically along a length of the second longitudinal axis; and
a support plate coupled to the second rack and located to support the peel specimen hangover tail,
wherein the first rack and the second rack are collinear along a horizontal axis extending substantially parallel to a longitudinal axis extending through a substantial length of the peel specimen.

17. The text fixture of claim 16,
wherein the first rack extends above a top face of the support plate that is configured to receive the peel specimen hangover tail and below a bottom face of the support plate that is opposed to the top face, and
wherein the second rack extends above the top face of the support plate and below the bottom face of the support plate.

18. The test fixture of claim 16, further comprising a gear train configured to drive the first and second racks, the gear train including at least two spur gears, one spur gear having twice as many teeth as the other spur gear.

19. The test fixture of claim 16, wherein the test fixture is configured to perform a T-peel test in which the peel specimen forms a T-like shape between symmetrical interfaces during operation of the test fixture with the peel specimen.

20. The text fixture of claim 16, wherein at least one of the upper grip and the lower grip are configured to hold the respective arm by grasping the respective arm of the peel specimen.

21. The test fixture of claim 20, wherein grasping the respective arm of the peel specimen further comprises clamping the respective arm of the peel specimen.

22. The test fixture of claim 16, further comprising:
a first gear driven by a first shaft, the first gear being coupled to the first rack and having a plurality of teeth;
a second gear driven by a second shaft, the second gear having a plurality of teeth that is twice the amount of teeth as the first gear; and
a third gear coupled to the second shaft and the second rack, the third gear having a plurality of teeth that is half the amount of teeth as the second gear such the second rack is driven in the vertical direction at one-half of the selected speed of the first rack.

23. The test fixture of claim 16, wherein the test fixture is configured such that testing of the peel specimen occurs in only a single mode.

24. The test fixture of claim 16, wherein the support plate is configured to support the hangover tail of the peel specimen by supporting the peel specimen across at least a quarter of the length of the peel specimen to suppress the effect of gravity.

* * * * *